United States Patent [19]

Shimizu et al.

[11] Patent Number: 5,719,679
[45] Date of Patent: Feb. 17, 1998

[54] METHOD AND APPARATUS FOR INSPECTING A ROTATING MEDICINE VIAL WITH CAMERAS

[75] Inventors: Koji Shimizu, Honjo; Kazumi Maruoka, Kamisato-machi, both of Japan

[73] Assignee: Eisai Co., Ltd., Tokyo, Japan

[21] Appl. No.: 519,185

[22] Filed: Aug. 25, 1995

[30] Foreign Application Priority Data

Sep. 1, 1994 [JP] Japan ................. 6-208502

[51] Int. Cl.$^6$ ............. G01N 21/90; G01N 21/00
[52] U.S. Cl. ............ 356/428; 356/427; 356/239; 356/240; 250/223 B; 250/224
[58] Field of Search .................. 356/427–428, 356/239–240; 250/223 B, 224

[56] References Cited

U.S. PATENT DOCUMENTS

| | | | |
|---|---|---|---|
| 3,627,423 | 12/1971 | Knapp et al. | 356/427 |
| 3,914,058 | 10/1975 | Knapp et al. | 356/427 |
| 4,063,823 | 12/1977 | Grat | 356/427 |
| 4,087,184 | 5/1978 | Knapp et al. | 356/427 |
| 4,549,205 | 10/1985 | Misaki et al. | 356/427 |
| 4,676,650 | 6/1987 | Bjorudal et al. | 356/427 |
| 4,804,273 | 2/1989 | Tondello et al. | 356/427 |
| 5,404,227 | 4/1995 | Sumita et al. | 356/428 |

FOREIGN PATENT DOCUMENTS 1152347  6/1989  Japan.

*Primary Examiner*—Frank G. Font
*Assistant Examiner*—Jason D Vierra Eisenberg
*Attorney, Agent, or Firm*—Griffin, Butler Whisenhunt & Kurtossy

[57] ABSTRACT

A method is for inspecting a vial in the course of conveying the vial by a rotary table, comprising the steps of inspecting the vial's lower half at a station of the vial's lower portion while the vial is rotated from above with its head being chucked, inspecting the vial's upper half at a station of the vial's upper portion while the vial is supported and rotated from below by a rotary belt adapted to be brought into contact with the vial, and combining these inspections of lower and upper halves to inspect the whole vial from its head to its bottom.

28 Claims, 17 Drawing Sheets

Fig. 17
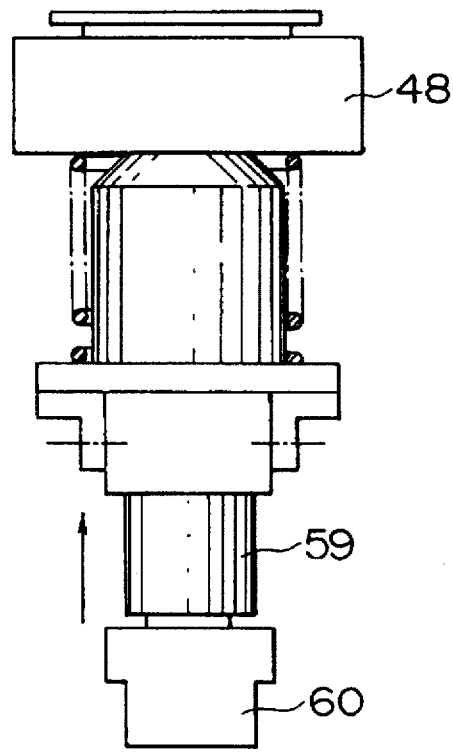
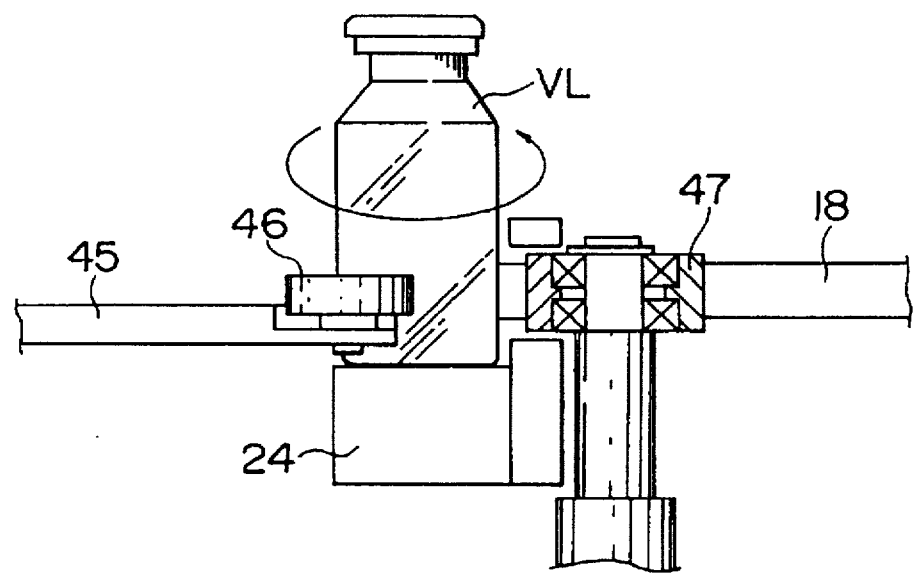

METHOD AND APPARATUS FOR INSPECTING A ROTATING MEDICINE VIAL WITH CAMERAS

BACKGROUND OF THE INVENTION

The present invention relates to a method and an apparatus for inspecting vials, particularly filled with freeze-dried medicine. The apparatus for such purpose is well known, for example, from the specification of Japanese Patent No.1993-59378, disclosing the apparatus comprising: an inspecting mechanism with illuminating means to project light beams to side and bottom bottom portions of a vial at inspecting zones provided on the course of each vial conveyance by a rotary member, CCD cameras to pick up various deficiencies such as crack, fissure (small crack), flaws of the vial, liquid spatter on the vial, deficient hooping of cap, deficient protector, stains and shortage of content, as corresponding images; an image processor adapted to digitalize these images for detection of the respective items of deficiency; and an inspecting mechanism with CCD cameras to pick up insufficient drying of medicine, dust on the surface of medicine and stains of medicine, with corresponding images and an image processor adapted to digitalize these images for detection of the respective items of deficiency.

However, the well known apparatus as mentioned above has a serious inconvenience that the light beams projected for inspection are partially obstructed by plural blocks supporting the vial, each block adapted to bear against a part of the vial so as to hold the vial suspended in midair under the effect of suction and vial rotating means provided at a plurality of locations outside the path along which said blocks supporting vials are conveyed and each adapted to come in contact with the side of each vial opposite to its side against which each vial supporting each block bears.

SUMMARY OF THE INVENTION

Accordingly, it is a principal object of the invention to provide method and apparatus for inspection of a vial presenting both the inspection of the vial's lower portion and the inspection of the vial's upper portion completely and continuously without being obstructed by a vial supporting block or mechanism.

The object set forth above is achieved, according to a primary aspect of the invention, by a method for inspection of a vial, said method comprising the steps of inspecting the vial's lower half while the vial is rotated with its head being chucked and inspecting the vial's upper half while the vial is supported and rotated from below, wherein the both steps are carried out in course of conveying the vial. According to a secondary aspect of the invention, the object set forth above is achieved with a high accuracy by a method for inspection of a vial, said method comprising steps of providing plural CCD cameras at optimum locations depending on respective deficiencies to be inspected and parallel processing images picked up by the CCD cameras as well as pixel counts and hereby continuously inspecting the whole vial from its head to its bottom.

The object set forth above is achieved, according to an aspect of the inventive apparatus, by an apparatus for inspection of a vial, said apparatus comprising a rotary table provided at stations with various inspections, a rotatable and vertically movable chuck of the parallel motion type or circular motion type provided at stations for inspecting a vial's lower portion such that the chuck may be pressed against the vial to chuck the vial, and a rotary belt provided at a station for inspecting a vial' upper portion so as to be brought in contact with the body of the vial.

The apparatus preferably has a mechanism for chucking the vial including a lower holder provided with anchor-shaped links adapted to be swung by a pusher and thereby to open and close the chuck fingers, an outer shaft, and an inner shaft connected to said pusher and adapted to be vertically moved together with the outer shaft and, after these shafts have been slidably moved over a predetermined distance, further slidably moved independently of said outer shaft.

The apparatus preferably has a mechanism for rotationally driving the outer shaft and a mechanism for vertically moving and closing the chuck comprising a combination of a mechanical valve and an air cylinder.

Reliability of inspection can be improved by providing the apparatus with an image processor to parallely process a plurality of images picked up by CCD cameras as well as pixel counts.

Efficiency of the apparatus can be improved by an arrangement such that a crack in a vial mouth, possibly generated due to hooping, which is normally invisible from outside can be directly inspected by projecting a light beam to the vial from its bottom so that the light beam can be propagated upward along the vial wall to the vial mouth and searching reflections of a light beam from the crack possibly present in the vial mouth with use of a camera directed obliquely upward.

In brief, the invention is characterized in that the vial's lower half is inspected at a station while the vial is rotated from above with its head being chucked and the vial's upper half is inspected at a station while the vial is supported and rotated from below by a rotary belt adapted to be brought into contact with the body of the vial, and wherein both steps are carried out in the course of conveying the vial by a rotary table and these steps of inspection are combined to inspect the whole the vial from its head to its bottom.

The reason why the vial's lower half is inspected first lies in that the vial content is very disturbable and it is preferred to inspect the surface of the vial content before the content is substantially disturbed in order to avoid erroneous detection of acceptable products and unacceptable products.

As for the effect of the invention, plural cameras can be provided at the optimum locations depending on respective deficiencies to be inspected and thereby the picked up images can be simultaneously and continuously processed in a high speed image processor. In addition, there are provided two steps of inspection, for instance, the inspection of vial's lower half while the vial is rotated from above with its head chucked and the inspection of vial's upper half while the vial is supported and rotated from below so that whole the vial can be inspected from its head to its bottom while the vial is rotated.

BRIEF DESCRIPTION OF THE DRAWINGS

The above and other objects of the invention will be seen by reference to the description taken in connection with the accompanying drawings, in which;

FIG. 17 is a front view showing a relationship in which the rotating mechanism for the vial body is operatively associated with the chuck mechanism for the vial head, with said chuck mechanism for the vial head not operating to chuck the vial head and said rotating mechanism for the vial body operating to rotate the vial body;

DESCRIPTION OF PREFERRED EMBODIMENTS

Details of the invention will be better understood from the following description of presently preferred embodiments, made in reference to the accompanying drawings.

Figure 1:
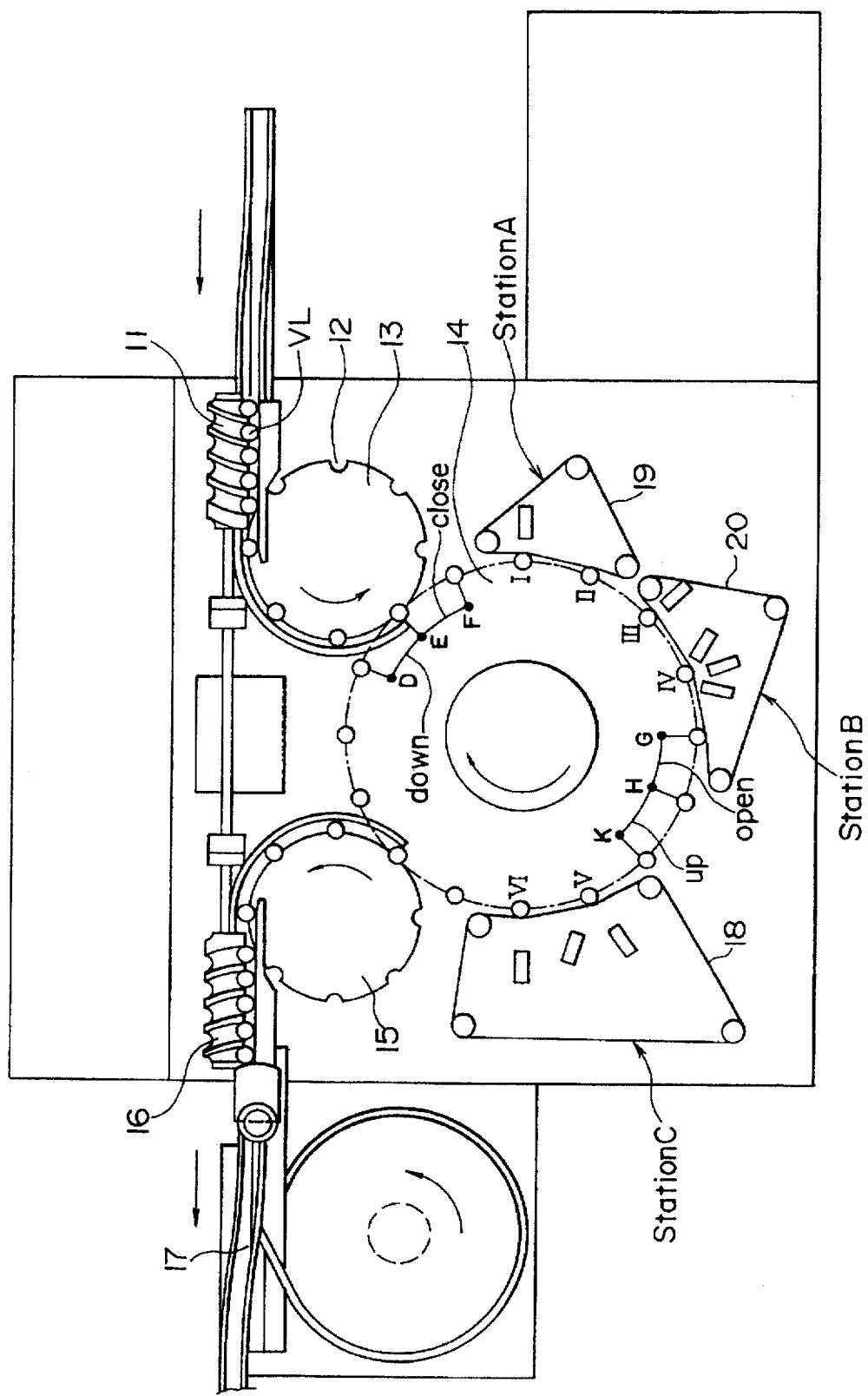
FIG. 1 is a plan view schematically showing steps of an inspecting method according to a specific embodiment of the invention.

FIG. 1 schematically shows steps of an inspecting method according to a specific embodiment of the invention. As shown in FIG. 1, Vials (VL) are successively conveyed by a screw conveyor (11) into recesses (12) formed in a periphery of a star wheel (13) and then rotation of said star wheel (13) causes these vials (VL) to be successively transferred to a rotary table (14) along which said vials (VL) have their lower portions inspected at an inspecting stations A and B, and have their upper portions inspected at an inspecting station C. The vials (VL) are successively transferred by a star wheel (15) to a screw conveyor (16) after they have been successively inspected, and then these vials (VL) are conveyed by said screw conveyor (16) to a product quality sorting conveyor (17).

While the specific embodiment as illustrated has been developed particularly in order to inspect vials filled with freeze-dried medicine, the invention is not limited to this specific embodiment. In general, a process of filling such vials with freeze-dried medicine comprises the steps of injecting a specified quantity of liquid medicine containing itemized pharmaceutical ingredients into an empty vial within a sterilized room; freeze-drying said liquid medicine; stoppering the vial with a rubber stopper after a quantity of air present within the vial has been replaced by $N_2$ gas; and finally, hooping the vial head with a ring-like cap around the vial head.

At the inspecting stations A and B, a chuck is lowered and closed to hold each vial at its head, and a pulley associated with the chuck holding said vial is rotated as said pulley is brought into contact with rotary belts (19) and (20), respectively. In association with the inspecting station C there is provided a rotary belt (18) adapted to be brought into contact with the body of each vial moved by the rotary table on a rail so as to rotate each vial. Mechanisms by which the vial is chucked and rotated will be described later more specifically.

The respective inspecting stations and aspects inspected at these stations are listed below in Table 1.

TABLE 1

Station A: assigned to inspect vial's lower portion.
Step I: inspects whether there is any foreign substance on the top face of freeze-dried medicine.
Step II: inspects whether there is any foreign substance on the bottom face of freeze-dried medicine.
Station B: assigned to inspect vial's lower portion.
Step III: inspects whether there is any foreign substance on the side faces of freeze-dried medicine.
Step IV: inspects (crack or flaw) the vial body, vial shoulder, and abnormal content of freeze-dried medicine. (absence or insufficiency of medicine content)
Station C: assigned to inspect the vial's upper portion.
Step V: inspects the vial's hooped head portion (e.g., breakage due to hooping)
Step VI: inspects the vial head (cap, aluminum hoop, vial neck).

Locations at which the respective steps of inspection as listed above are conducted are indicated in FIG. 1.

Figure 4:
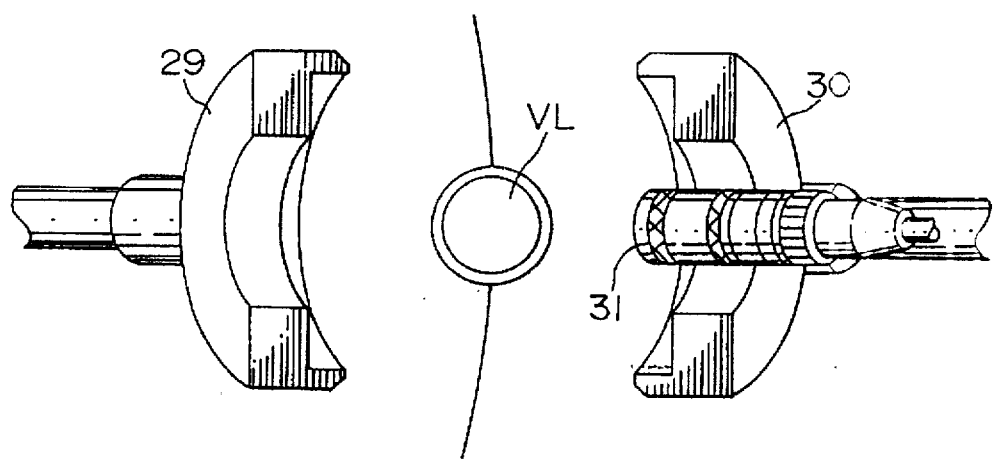
FIG. 4 is an isometric view schematically showing a manner in which a step I of lower portion inspection is conducted in the proximity of an inspecting station A indicated in FIG. 1.
Figure 5:
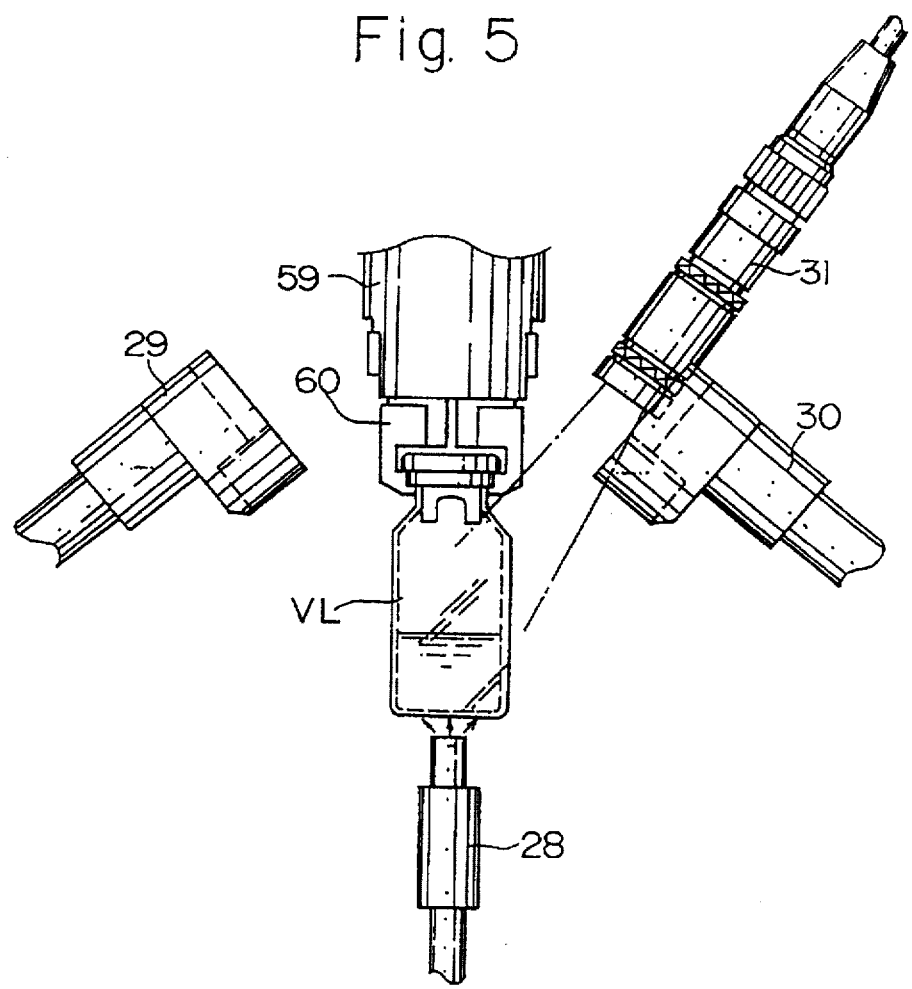
FIG. 5 is a front view corresponding to FIG. 4.

FIGS. 4 and 5 illustrate the manner in which the step I of inspecting the vial's lower portion as indicated above in Table 1 is carried out. During this step, the vial is held by the chuck at its head and rotated for inspection and therefore there is no need to provide a rail to support and guide the vial. A light beam from light (28) is directed to the vial (VL) from below, taking care to avoid shadows from cracks in the freeze-dried medicine reaching the top surface of the medicine so that the inspection may be free from an adverse affects thereof. To this end, the vial (VL) is exposed to light beams emitted from semicircular ring lights (29), (30) located in and outside the rotary table (14), and a camera (31) located obliquely above the vial (VL) picks up an image of the vial (VL). In this manner, an image of foreign substance, if it is present on the top face of the freeze-dried medicine, will be directly detected.

Figure 6:
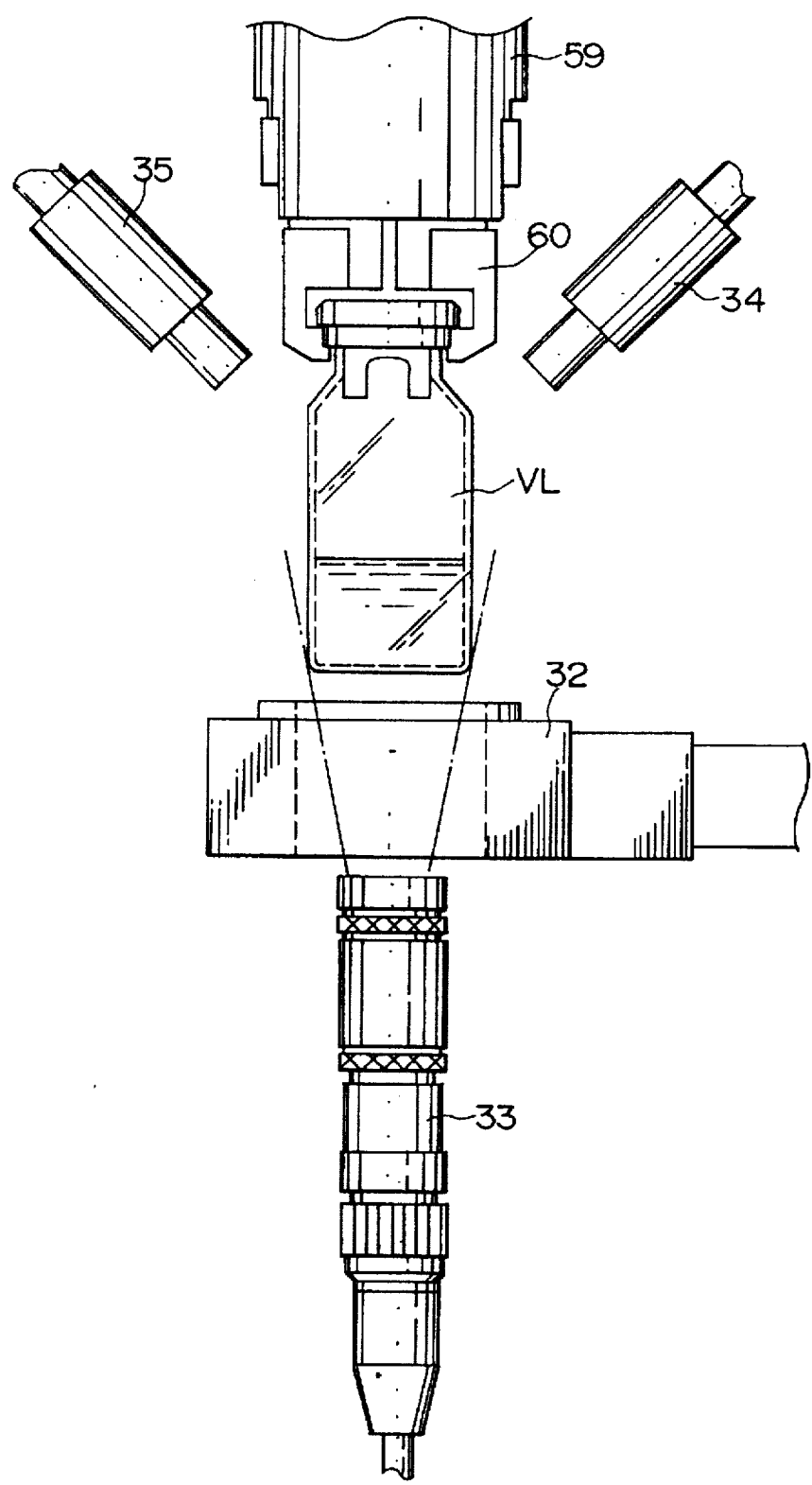
FIG. 6 is a front view schematically showing a step II of lower portion inspection conducted in the proximity of an inspecting station A indicated in FIG. 1.

FIG. 6 illustrates a manner in which the step II of inspecting the lower portion indicated above in Table 1 is conducted. This step II also requires no rail to support the vial (VL) from below, since the vial (VL) is held by the chuck and rotated for inspection. Specifically, the vial (VL) is exposed to light beams emitted from light sources (35), (34) located obliquely thereabove in and outside the rotary table (14) in order to avoid the difficulty that the inspection might be affected by cracks in the freeze-dried medicine while the vial (VL) is illuminated by a ring light (32) located below the vial (VL) so that an image of foreign substance, if it is present on the bottom face, can be directly picked up by a camera (33) located below the vial (VL).

Figure 7:
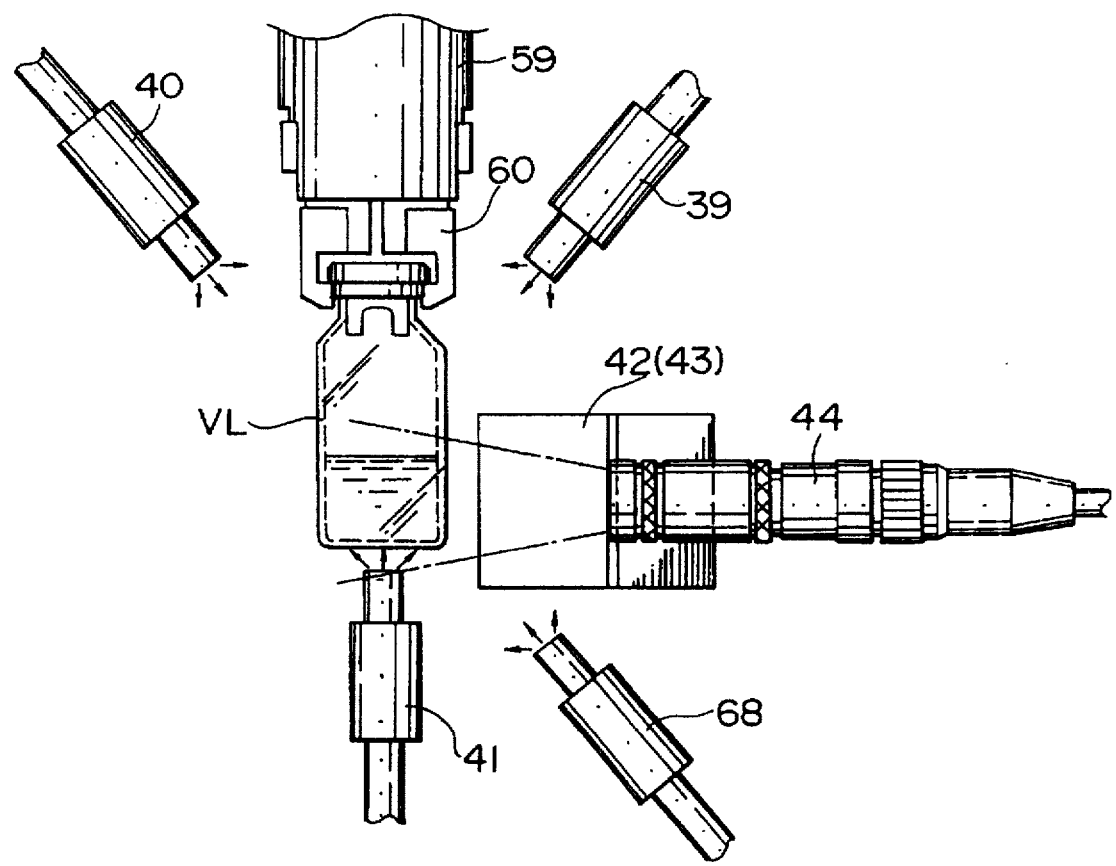
FIG. 7 is a front view schematically showing a step III of lower portion inspection conducted in the proximity of an inspecting station B indicated in FIG. 1.
Figure 8:
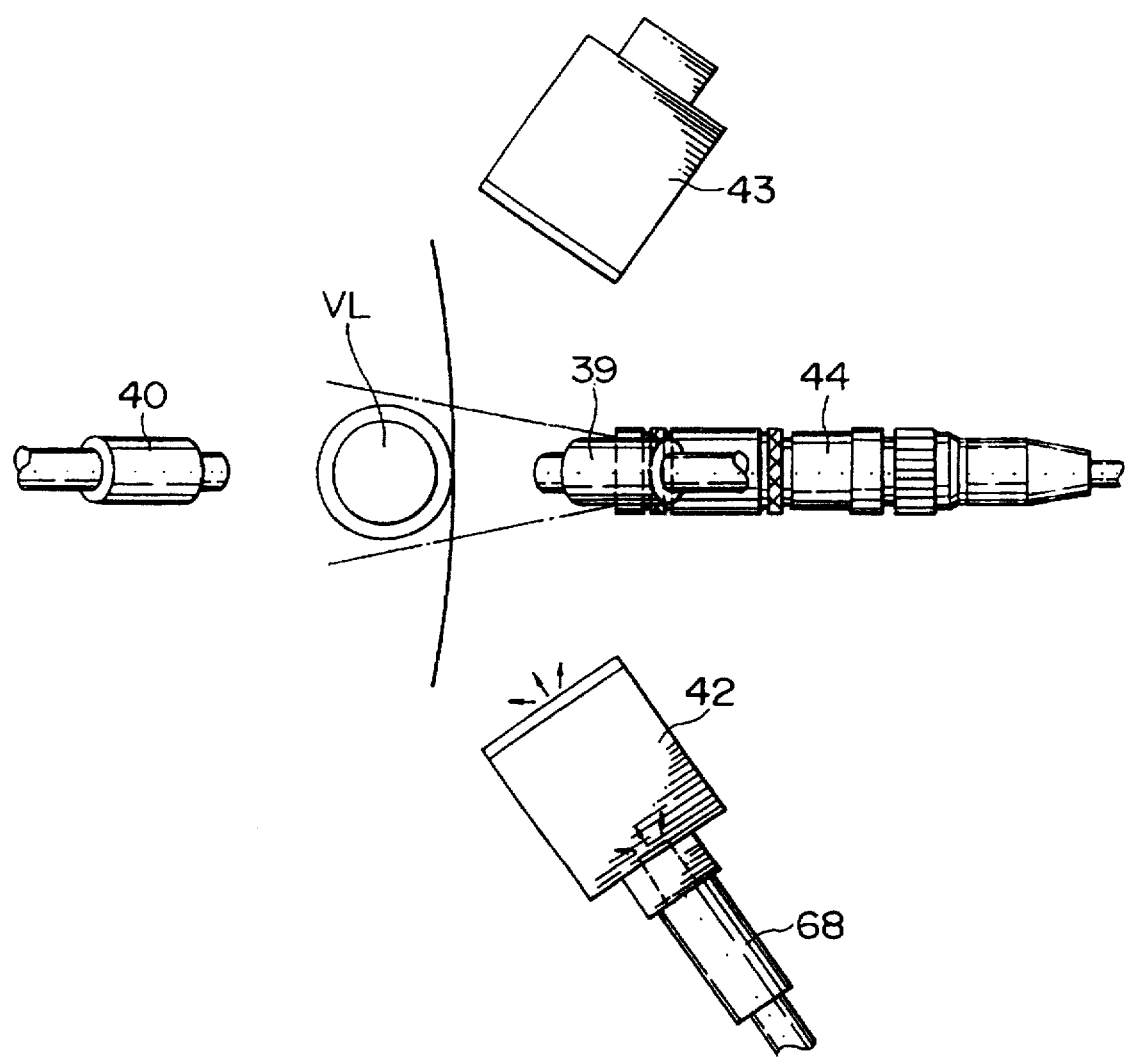
FIG. 8 is a plan view corresponding to FIG. 7.

FIGS. 7 and 8 illustrate a manner in which the step III of inspecting the lower portion indicated in Table 1 is conducted. As illustrated, the body of the vial (VL) is exposed to light beams emitted from light sources (39), (40) located obliquely above the vial (VL) in and outside the rotary table (14), and a light source (68) located obliquely below the vial (VL) while the vial (VL) is exposed to light beams horizontally projected from diffusion lights (42),(43) located laterally of the vial (VL) so that an image of foreign substance, if it is present on the side face, can be directly picked up by a camera (44) located laterally of the vial (VL) without any difficulty that the inspection might be affected by shadows of irregularities formed due to cracks in freeze-dried medicine.

Figure 9:
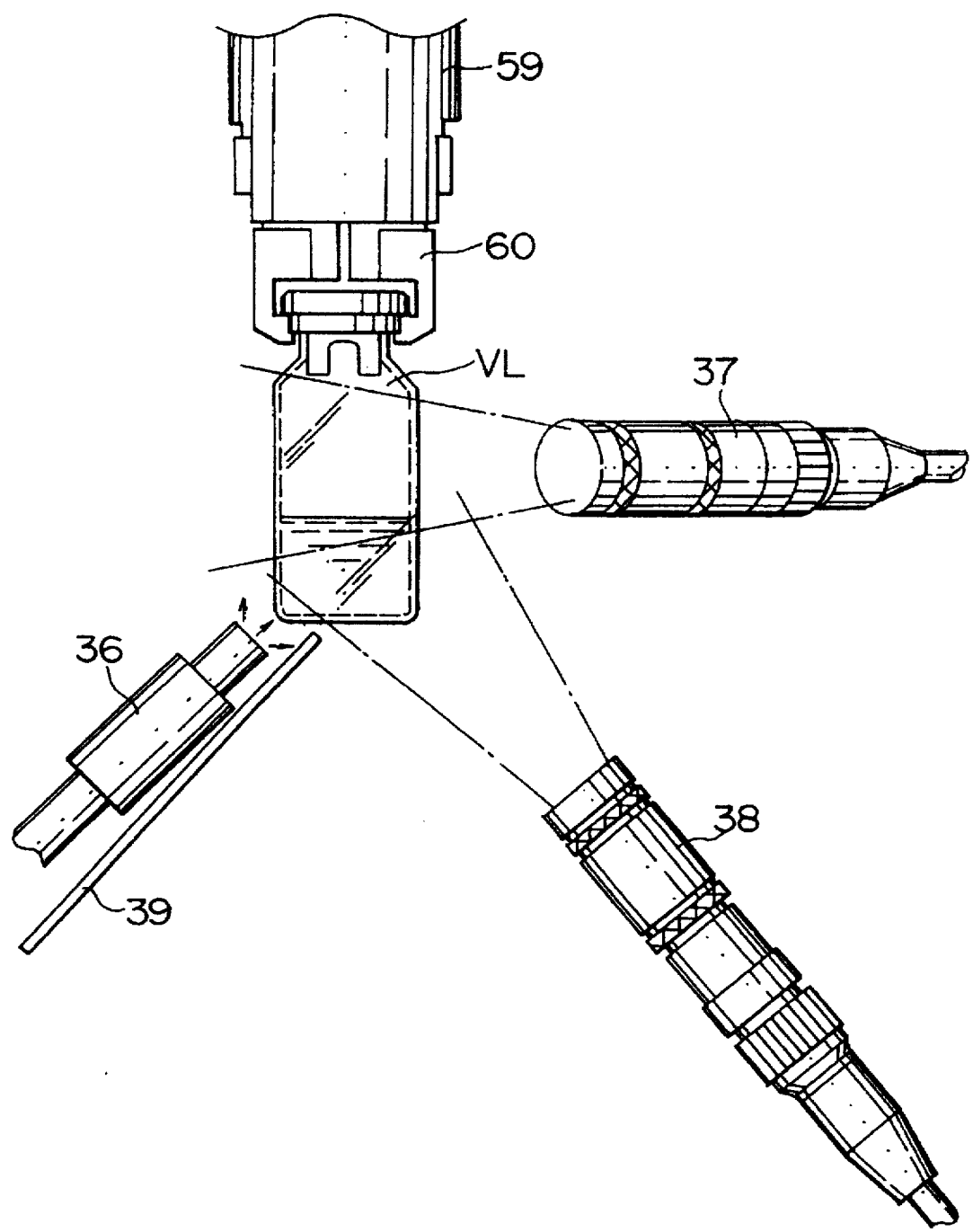
FIG. 9 is a front view schematically showing a step VI of lower portion inspection conducted in the proximity of the inspecting station B indicated in FIG. 1.
Figure 10:
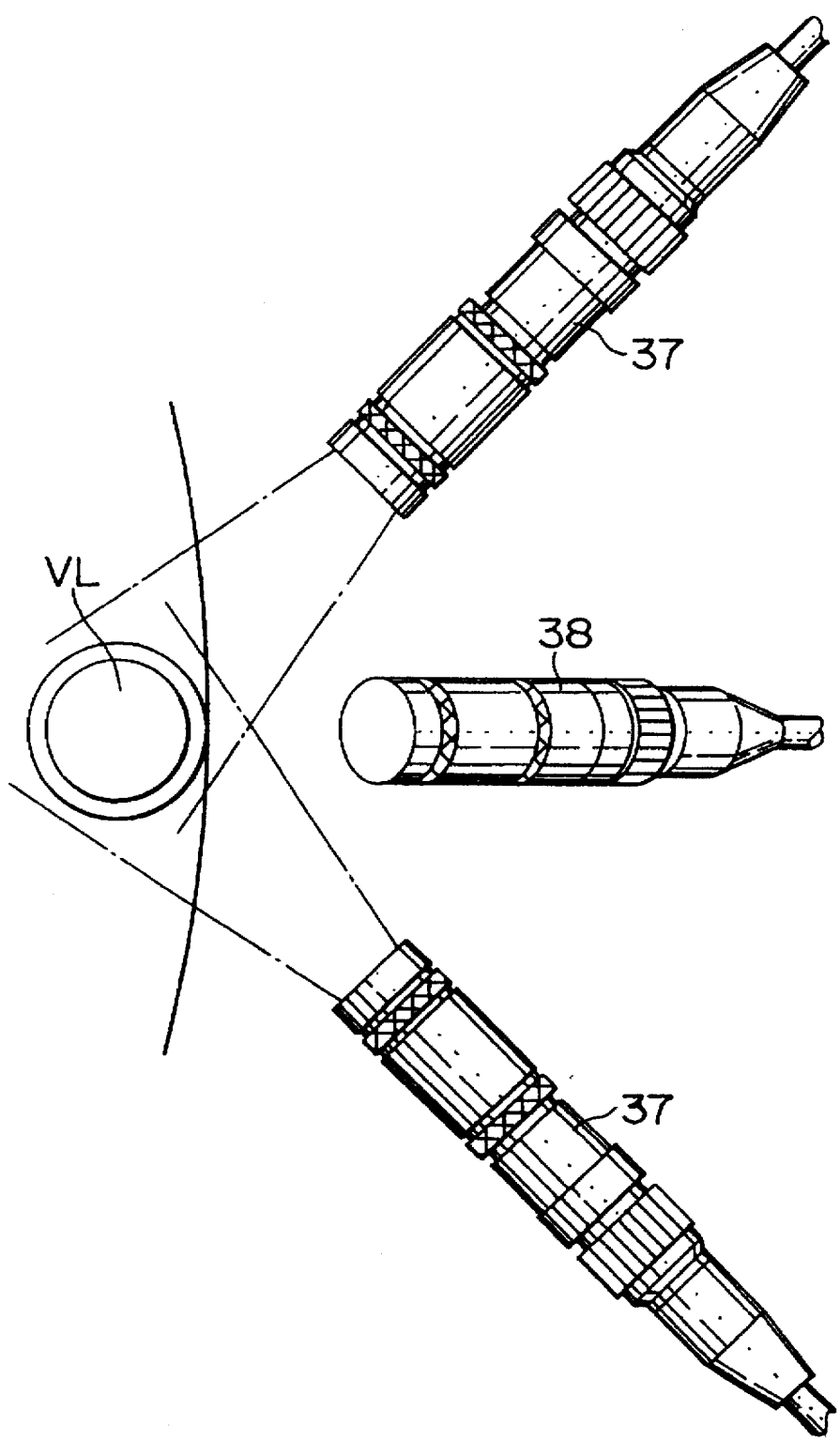
FIG. 10 is a plan view corresponding to FIG. 9.

FIGS. 9 and 10 illustrate a manner in which the step IV of inspecting the lower portion indicated above in Table 1 is conducted. As illustrated, the vial (VL) is exposed to a light beam emitted from a light source (36) located obliquely below the vial with a douser (39) extending below this light source (36) in order to prevent said light beam from directly reaching cameras (37),(38) located on either side of and obliquely below the vial (VL) so that these cameras (37), (38) may reliably pick up breakage in the body or the neck of the vial (VL), empty vials and abnormal content of freeze-dried medicine.

Figure 11:
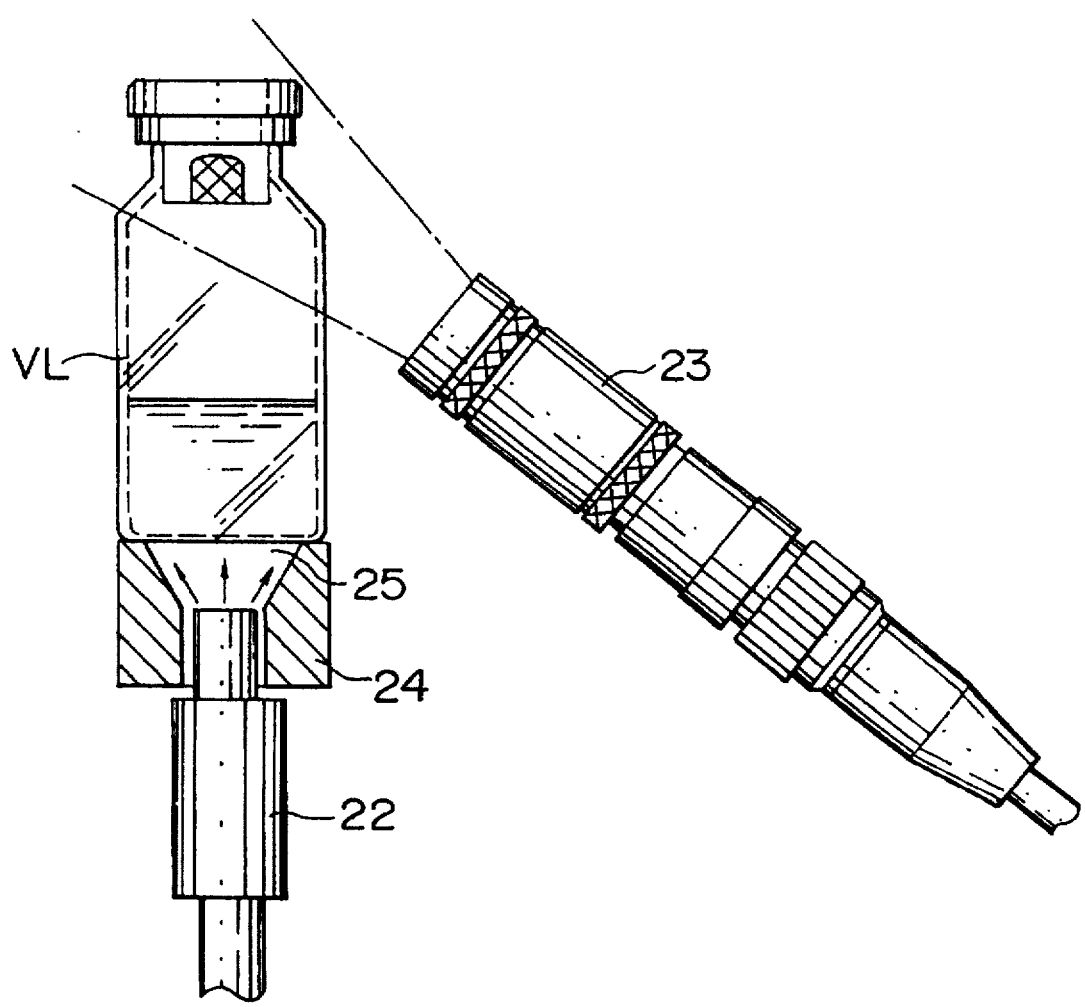
FIG. 11 is a front view schematically showing a step V of upper portion inspection conducted in the proximity of an inspecting station C indicated in FIG. 1.
Figure 12:
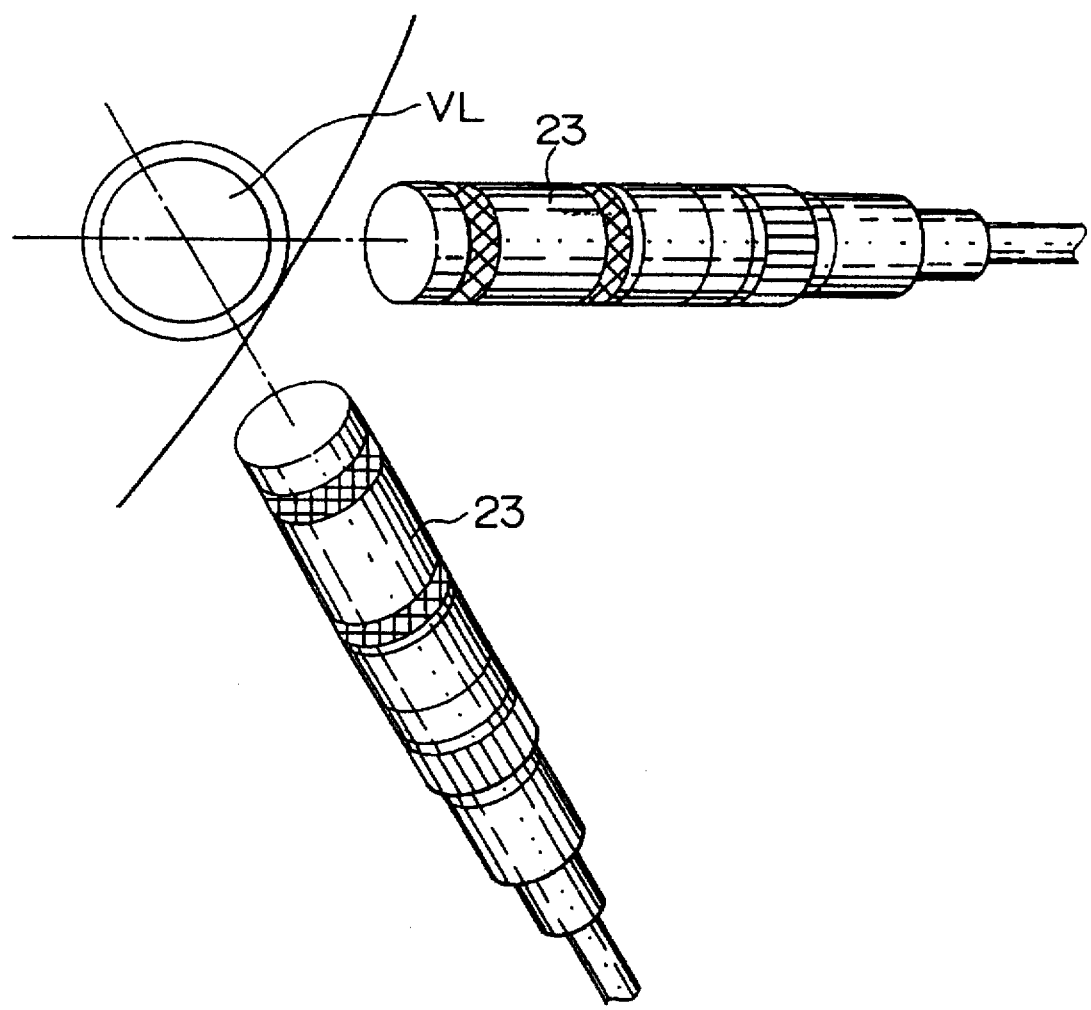
FIG. 12 is a plan view corresponding to FIG. 11.

FIGS. 11 and 12 illustrate a manner in which the step V of inspecting the upper portion indicated above in Table 1, wherein the vial (VL) is exposed to a light beam projected from a light source (22) located below the vial (VL) through a slit (25) of a rail (24) so that the light beam can be propagated along the vial wall and, if there is a crack around the vial vial, the light reflected by this crack can be directly picked up by a camera (23) directed obliquely upward. In this manner, a breakage due to hooping of the vial can be detected.

Figure 13:
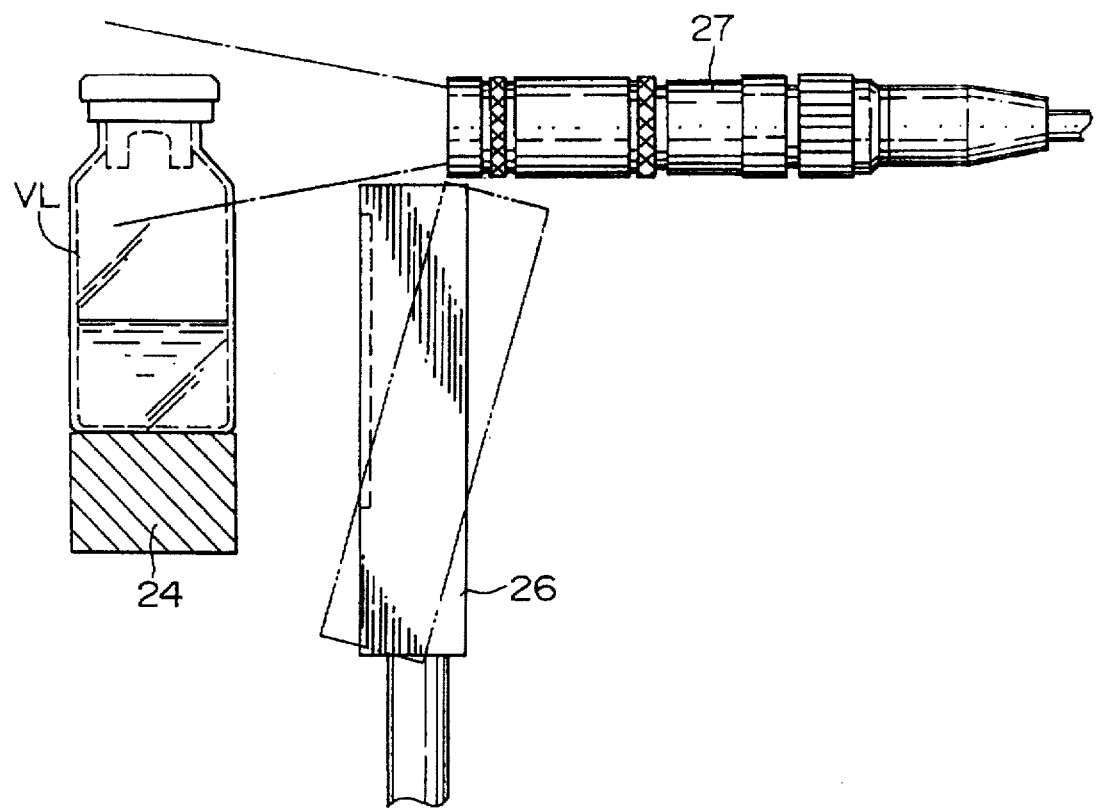
FIG. 13 is a front view schematically showing a step VI of upper portion inspection conducted in the proximity of the inspecting station C indicated in FIG. 1.
Figure 14:
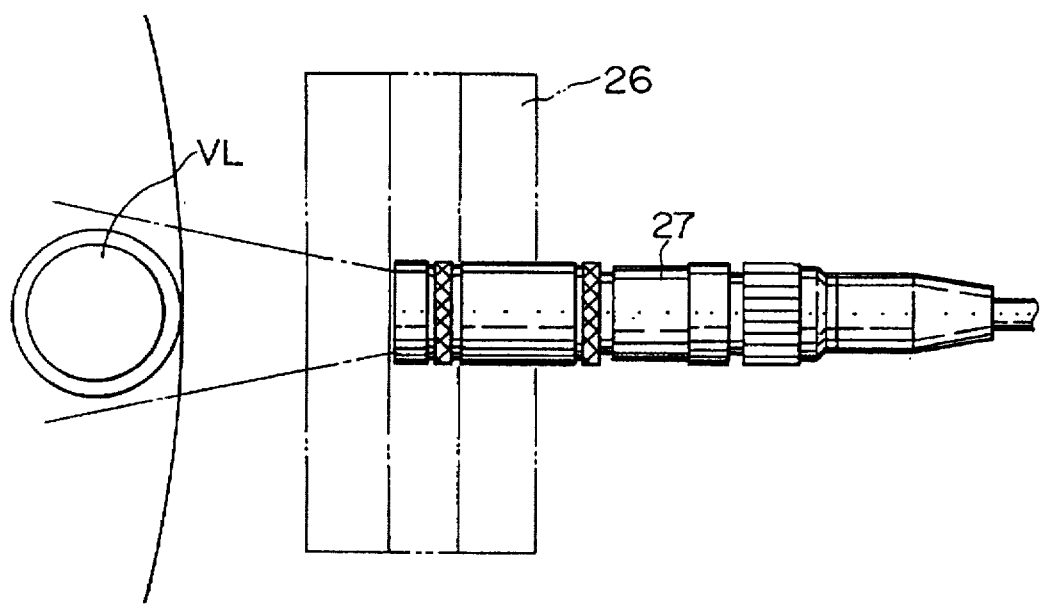
FIG. 14 is a plan view corresponding to FIG. 13.

FIGS. 13 and 14 illustrate a manner in which the step VI of inspection indicated above in Table 1 is conducted, wherein the vial (VL) is exposed to diffused light projected from a light source (26) located laterally of the vial (VL) and light beams reflected from the vial head are picked up by a camera (27) located laterally of the vial (VL) to inspect any deficiency of the head, aluminum hoop or vial neck. It should be understood that the light source (26) is tiltable within a limited angle. It should be also understood that the items to be inspected are not limited to those as have been mentioned and additional locations for inspection may be separately provided to increase the number of items, for example, deficiency of molding. Furthermore, the position as well as the number of cameras or lights may be adjusted or changed depending on size and shape of the vial to be inspected.

Figure 2:
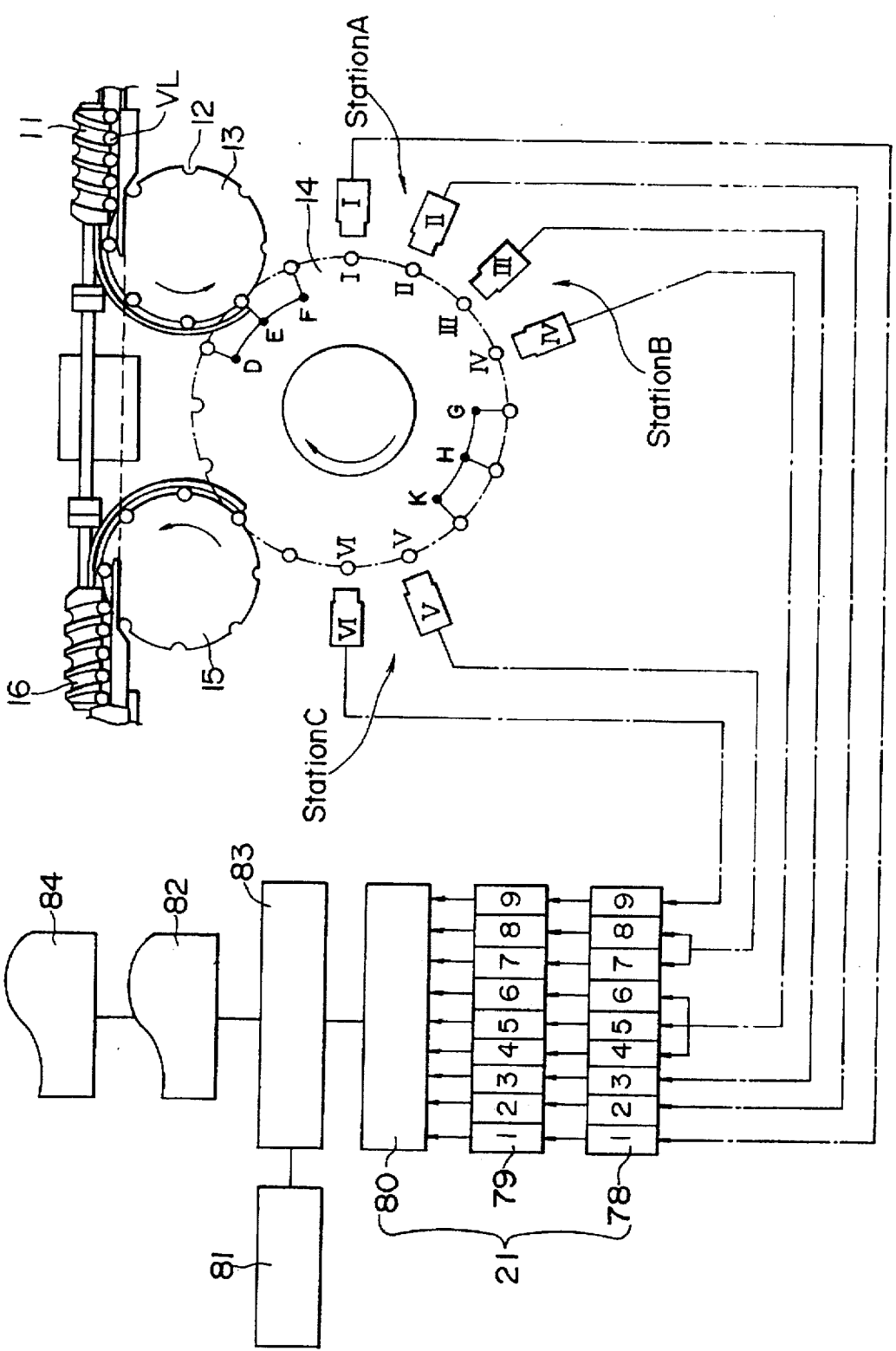
FIG. 2 is a system diagram showing a procedure in which images picked up by respective cameras are processed according to the inspecting method of the invention.
Figure 3:
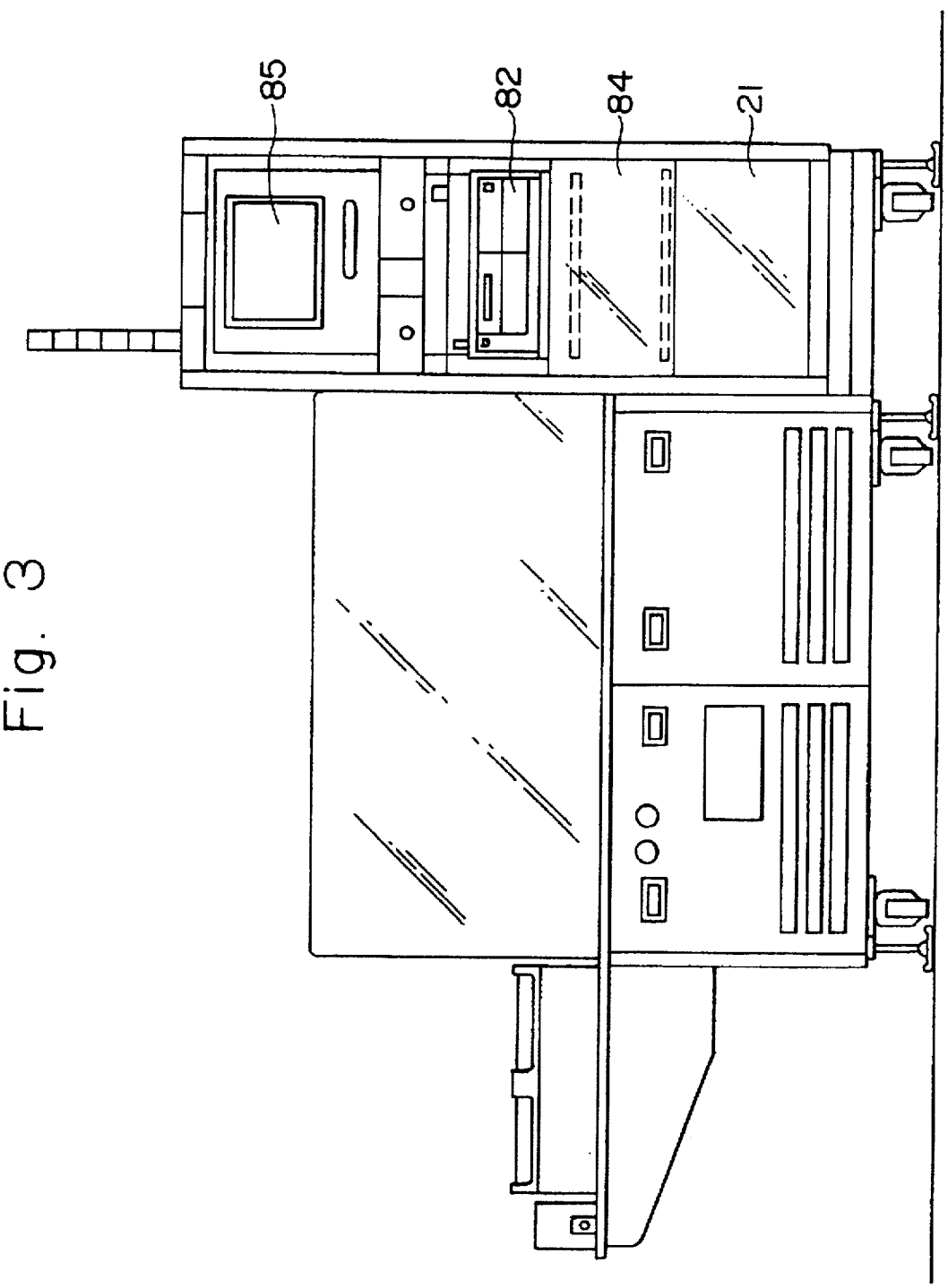
FIG. 3 is a front view of an apparatus for carrying out the steps corresponding to FIG. 1.

The images picked up by the respective cameras during these step I through VI of inspection are continuously input to an image processor (21) as shown by FIG. 2 by a single field (1/60) at a time, said image processor (21) including an extradition circuit (78) and a high speed processor (79) adapted to identify individual patterns. The images can be processed in parallel by an arithmetic circuit (80) included in the image processor with a pair of memories being alternately shifted, allowing continuous decisions to be made by the single field at a time. Results of an inspection can be output via a personal computer (82) to a printer (84) or displayed on a touch panel monitor (85) shown in FIG. 3.

When plural windows are defined within a visual field of each camera, a binary coded level can be set for every window and therefore the sensitivity can be optimized for every deficiency. It should be understood that the respective windows may be defined also to overlap one another.

It has conventionally been impossible for the prior art to achieve continuous processing of the picked up images, since a determined processing time is taken from the time point at which the images have been input to the image processor to the time point at which the results are output. On the contrary, the unique arrangement according to the invention as has been described above makes the continuous processing possible. The mechanism used to rotate the vial body during the steps V–VI of inspecting the upper portion and the mechanism used to chuck the vial head during the steps I through VI of inspecting the lower portion will be now described.

Figure 15:
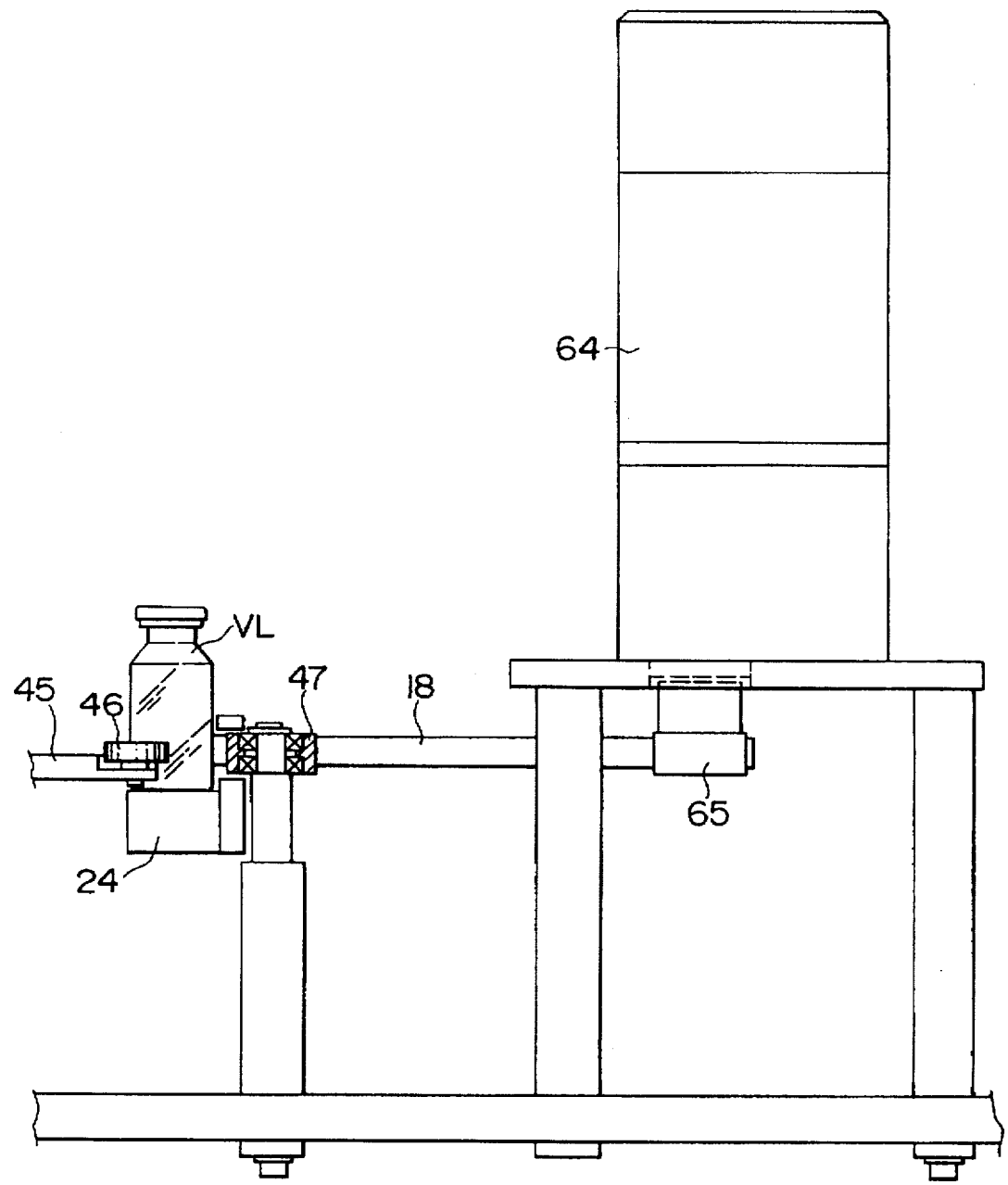
FIG. 15 is a front view showing a mechanism used to rotate a vial body during the steps V and VI of upper portion inspection conducted in the proximity of the inspecting station C indicated in FIG. 1.

First, the mechanism used to rotate the vial body during the steps V–VI is illustrated in FIG. 15. At the inspecting station C in FIG. 1, the vial (VL) is held between a pair of press rollers (46), (46) carried by a holder adapted to be rotated coaxially with the rotary table (14) and guided on the rail (24). The vial (VL) is brought into contact with a rotary belt (18) driven by pulleys (65),(47) operatively associated with an electric motor (64) and thereby the vial (VL) is rotated. While the vial (VL) is in contact with the rotary belt (18) and thereby rotated, the chuck mechanism for the vial head remains lifted above the vial (VL) as seen in FIG. 17.

Figure 16:
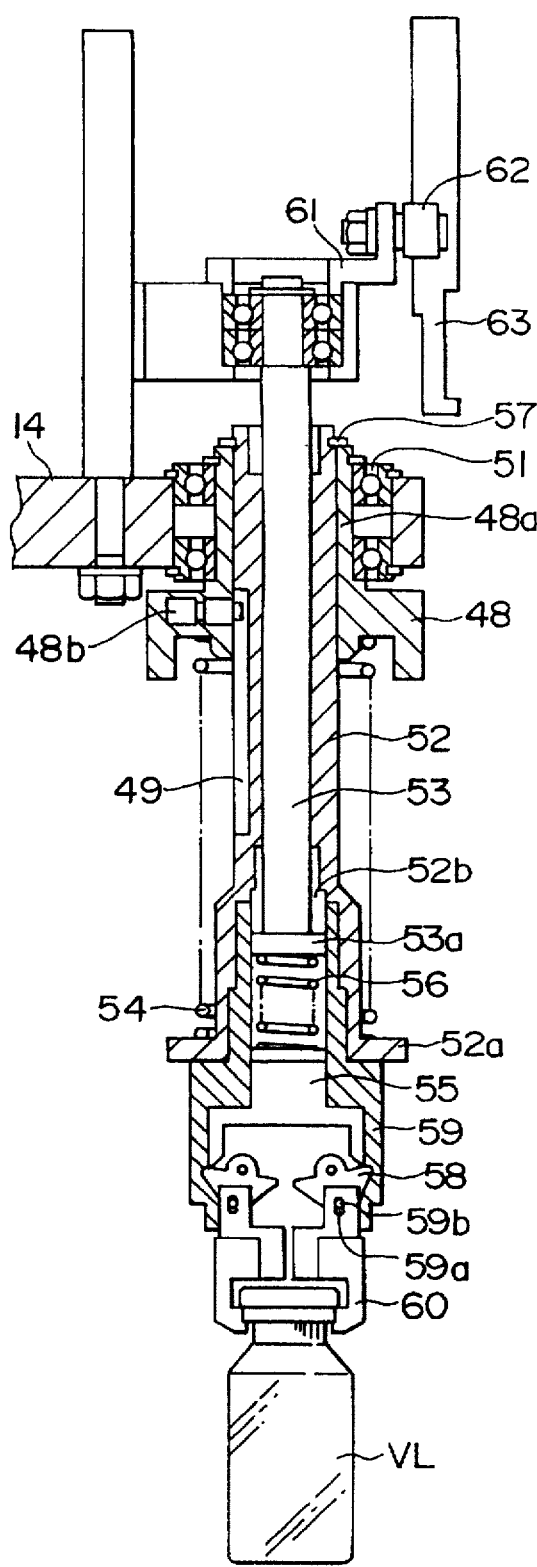
FIG. 16 is a front view showing a chuck mechanism for a vial head used during the steps I through IV of lower portion inspection conducted at the inspecting stations A and B indicated in FIG. 1.
Figure 18:
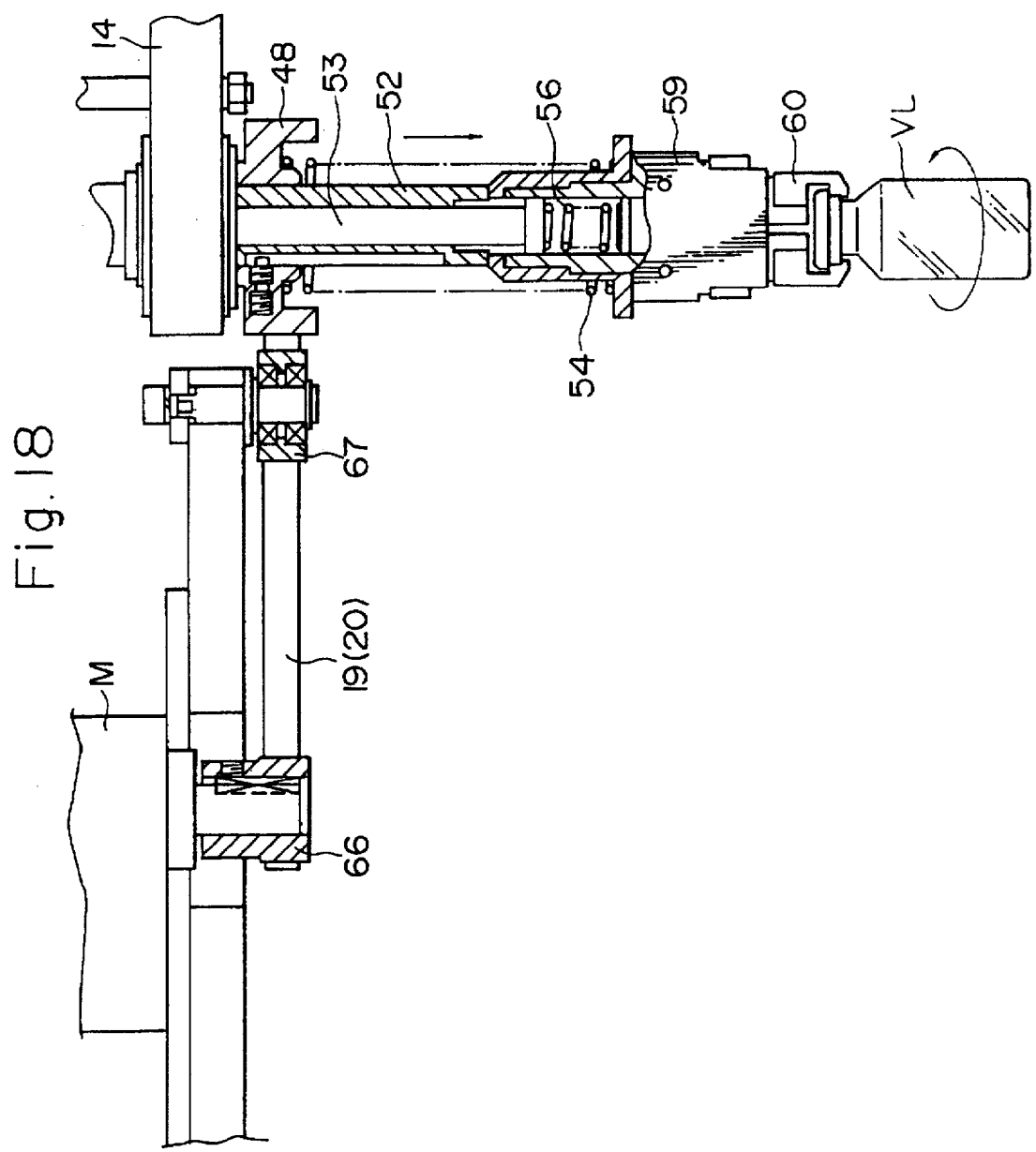
FIG. 18 is a front view showing the chuck mechanism for vial head operating to chuck the vial head.

FIG. 16 shows a specific embodiment of the chuck mechanism for the vial head used during the steps I through VI of inspecting lower portion. As shown, a boss (48a) of a pulley (48) is rotatably supported by the rotary table (14) with interposition of a bearing (51). The pulley (48) is rotated as it is brought into contact with belts (19), (20) draped between and about a pulley (66) driven by an electric motor (M) and a pulley (67) as shown by FIG. 18. The pulley (48) has a pin (48b) adapted to be slidably engaged with a slit (49) of an outer shaft (52) which contains, in turn, an inner shaft (53) coaxially extending therein. Said outer shaft (52) can be slidably lifted under control by said pin (48b) along a vertical length of said slit (49).

A spring (54) is disposed between a flange (52a) of the outer shaft (52) and the pulley (48) and a spring (56) is disposed between the flange (53a) of the inner shaft (53) and a pusher (55).

The outer shaft (52) is provided adjacent its uppermost portion with a stopper (57) adapted to be engaged with the boss (48a) of the pulley (48).

Below the flange (52a) of the outer shaft (52) there is provided a holder (59) and chuck fingers (60).

The holder (59) surrounds the pusher (55) adapted to be actuated by the flange (53a) of the inner shaft (53) cooperating with the spring (56) and the pusher (55) normally bears against respective action levers (58). The action levers (58) have their pivot pins (59a) pivotally supported by slits (59b) of the associated chuck fingers (60) so that the chuck fingers (60) cooperate with the respective action levers (58) so as to function as anchor-shaped links and to form a chuck of parallel motion type. The inner shaft (53) is provided adjacent its uppermost portion with an arm (61) carrying a cam follower (62) adapted to be engaged with a groove-shaped cam (63) provided above and around the rotary table (14). The chuck mechanism for vial head as has been described above operates as follows:

The groove-shaped cam (63) causes the outer shaft (52) and the inner shaft (53) to be lowered. The outer shaft (52)

has been lifted against a biasing force of the spring (54) and is lowered as it is released from this biasing force. The inner shaft (53), on the other hand, is directly coupled to the cam follower (62) and adapted to be vertically moved by the groove-shaped cam (63).

Lowering of the outer shaft (52) is stopped as the stopper (57) on the outer shaft (52) is engaged with the boss (48a) of the pulley (48) during such downward movement of these shafts (52),(53). However, the inner shaft (53) is further lowered within the outer shaft (52) against a biasing force of the spring (56), causing the pusher (55) to swing the action levers (58) and thereby the chuck fingers (60) are closed so as to chuck the vial. Rotational force transmitted to the pulley (48) during such phase of operation causes the outer shaft (52) to be rotated through engagement between the pin (48b) of the pulley (48) and the slit (49) and thereby causes also the holder (59) formed on the outer shaft (52) from being lifted, but the flange (53a) biased by the spring (56) is lifted and comes into engagement with a stepped portion (52b) of the outer shaft (52) as well as the chuck fingers (60) to be rotated.

The operation as has been described above will be discussed in reference with FIG. 1. Lowering of the chuck fingers (60) occurs along the course defined between a point D and a point E and closure of the chuck fingers (60) occurs along the course defined between the point E and a point F as shown in FIG. 1. While the inner shaft (53) is being lifted by the groove-shaped cam (63), the spring (54) tends to prevent the outer shaft (52) from being lifted, but the flange (53a) of the inner shaft (53) biased by the spring (56) to be lifted comes in engagement with a stepped portion (52b) of the outer shaft (52) and thereby lifts the outer shaft (52) together with the inner shaft (53) against the biasing force of the spring (54). The pusher (55) is released from a pressure exerted by the flange (53a) thereupon as the inner shaft (53) begins to be lifted. Thereupon, the action leavers (58) release the chuck fingers (60) which are then opened under a biasing force of a spring (not shown) disposed between these chuck fingers (60). Consequently, the vial is released from the chuck fingers (60).

Referring to FIG. 1, after the vial has been released from the chuck fingers in this manner along the course defined between a point G and a point H, lifting of the chuck occurs again along the course defined between the point H and a point K.

While the invention has been described hereinabove as employing the chuck of parallel motion type, it is also possible to employ a chuck of circular motion type adapted to be vertically moved by a combination of a mechanical valve and an air cylinder.

Figure 19:
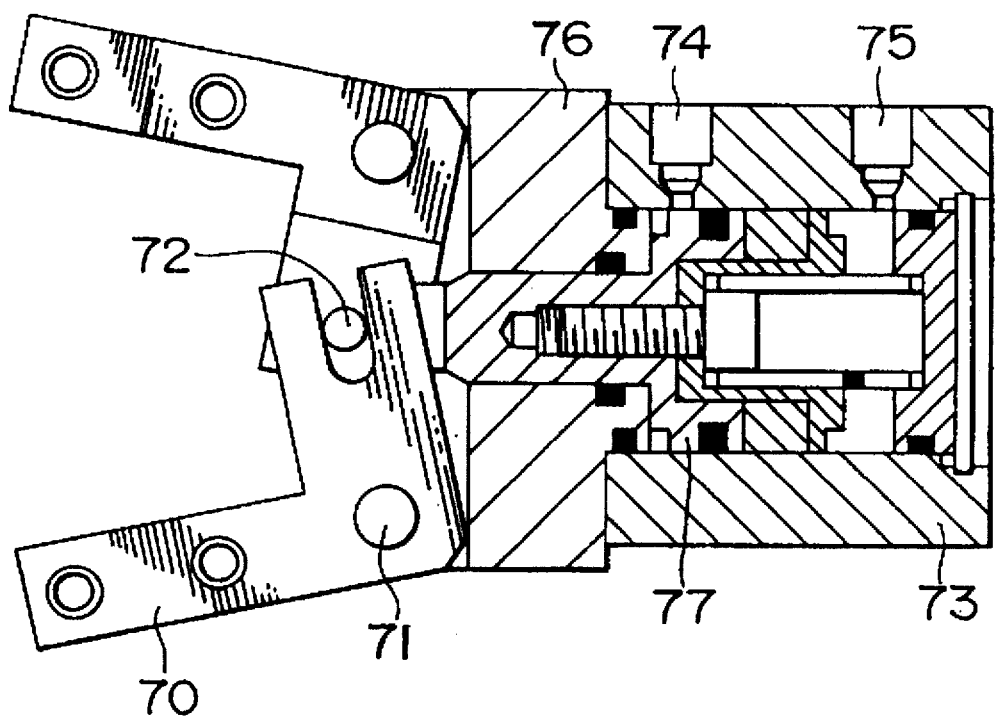
FIG. 19 is a side view showing a variant of the chuck mechanism for the vial head.

Such chuck of circular motion type is shown in FIG. 19. A master jaw (70) is swung around its pivot pin (71) as an actuating pin (72) is moved back and forth, and the actuating pin (72) is moved back and forth, in turn, by a piston rod of an air cylinder (73). The piston rod is moved back and forth, in turn, by air supply/exhaust occurring through air inlet/outlet (74) (75) into/from a space defined in front of or behind the piston (77).

Air supply is controlled by the mechanical valve.

Any alternative arrangement may be adopted for the invention so far as the chuck can be opened and closed appropriately in operative association with vertical movement thereof. For example, a cylindrical cam as the chuck is also adoptable.

The stations at which the lower portion of each vial is inspected with its head held by the chuck include no rail (24) to support this vial and the station at which the upper portion of each vial is inspected includes the rail (24) provided under the vial to support it.

As will be apparent from the foregoing description, the invention is characterized in that the single rotary table can be effectively utilized in the course of conveying the vials not only for inspection of vial's lower half during which the vial is rotated with its head while being chucked but also for inspection of vial's upper half during which the vial is supported from below and rotated; and one or more CCD cameras provided on the optimum locations depending on the respective deficiencies to be inspected and the picked up images as well as the pixel counts are processed in parallel so that the whole vial can be continuously inspected from its head to its bottom.

A crack in the vial mouth due to hooping which normally can not be visually detected from above can be optically inspected by illuminating the vial from its bottom so that the light can be propagated upward along the vial wall to the vial mouth and searching reflections of the light on a crack present in the vial mouth with use of the camera directed obliquely upward.

While the invention has been particularly shown and described with reference to preferred embodiments thereof, it will be understood by the skilled in the art that the foregoing and other changes in form and details can be made therein without departing from the spirit and scope of the invention.

What is claimed is:

1. A method for inspecting a vial comprising a body and a head and having a content therein, and wherein the inspection is completed and continuously achieved without being obstructed by a vial supporting mechanism, and wherein the inspection includes inspection of a lower portion of the vial and inspection of an upper portion of the vial, comprising:

1) applying a chuck to the head of the vial so as to grasp the head and suspend the vial;
2) rotating the chuck so as to rotate the suspended vial;
3) illuminating the vial with at least one light while the vial is rotated by the chuck;
4) imaging the illuminated vial with at least one camera and displaying the image;
5) inspecting the lower portion of the vial from the displayed image for abnormal contents, foreign substances on faces on the content and defects in the vial body;
6) releasing the chuck and placing the vial on a support which contacts the bottom of the vial;
7) rotating the vial while on the support;
8) illuminating the vial with at least one light while the vial is rotated on the support;
9) imaging the illuminated vial with at least one camera and displaying the image; and
10) inspecting the upper portion of the vial from the displayed image for defects in the vial head.

2. The method of claim 1, wherein the illumination of step 3 is at least from obliquely below the vial and the camera is located obliquely below the vial such that defects in the vial body are detectable.

3. The method of claim 1, wherein the content is a freeze-dried medicine.

4. The method of claim 3, wherein the illumination of step 3 is at least from below a bottom of the vial and the camera is located obliquely above the vial such that at least foreign substances at a top face of the content are detectable.

5. The method of claim 3, wherein the illumination of step 3 is at least from obliquely above the vial and the camera is located below the vial such that at least foreign substances at a bottom face of the content are detectable.

6. The method of claim 3, wherein the illumination of step 3 is at least from obliquely above the vial and the camera is located laterally of the vial such that at least foreign substances at side faces of the content are detectable.

7. The method of claim 3, wherein the illumination of step 3 is at least from obliquely below the vial and the camera is located obliquely below the vial such that at least abnormal contents are detectable.

8. The method of claim 3, wherein the illumination of step 8 is at least below the vial bottom such that light can propagate along vial walls and the camera is located obliquely upwardly toward the vial head such that at least defects in a mouth of the vial are detectable.

9. The method of claim 1, wherein the illumination of step 8 is at least laterally of the vial such that light is reflected from the vial head and the camera is located laterally of the vial such that at least defects in the vial head are detectable.

10. The method of claim 1, wherein the imaging is performed at separate inspection stations, with each inspection station having different spacial arrangements of the illumination and camera.

11. The method of claim 10, wherein the inspection stations are spaced about a rotatable wheel which conveys the vial from station to station.

12. The method of claim 1, wherein there are a plurality of CCD cameras and lights.

13. An apparatus for inspecting a vial comprising a body and a head and having a content therein, and wherein the inspection is completely and continuously achieved without being obstructed by a vial supporting mechanism, and wherein the inspection includes inspection of a lower portion of the vial and inspection of an upper portion of the vial, comprising:

1) a chuck configured to releasably grasp the head of the vial and suspend the vial;

2) chuck rotation means for rotating the chuck so as to rotate the vial while being suspended;

3) at least one first light for illuminating the vial while the vial is being rotated by the chuck;

4) at least one first camera for imaging the illuminated vial and display means for displaying the image such that the display will show in the lower portion of the vial any abnormal contents, foreign substances on the face of the content, and defects in the vial body;

5) releasing means for releasing the chuck and releasing the vial;

6) a support for supporting the bottom of the released vial;

7) vial rotation means for rotating the vial while supported by the support;

8) at least one second light for illuminating the vial while the vial is being rotated;

9) at least one second camera for imaging the illuminated vial and display means for displaying the image such that the display will show in the upper portion of the vial defects in the vial head; and 10) a rotatable table for moving the vial to and from successive inspection stations.

14. The apparatus of claim 13, wherein the first light is positioned at least obliquely below the vial and the first camera is located obliquely below the vial such that defects in the vial body are detectable.

15. The apparatus of claim 13, wherein the content is a freeze-dried medicine.

16. The apparatus of claim 15, wherein the first light is at least disposed below a bottom of the vial and the camera is located obliquely above the vial such that at least foreign substances at a top face of the content are detectable.

17. The apparatus of claim 15, wherein the first light is at least disposed obliquely above the vial and the camera is located below the vial such that at least foreign substances at a bottom face of the content are detectable.

18. The apparatus of claim 15, wherein the first light is at least disposed obliquely above the vial and the camera is located laterally of the vial such that at least foreign substances on side faces of the content are detectable.

19. The apparatus of claim 15, wherein the first light is at least disposed obliquely below the vial and the camera is located obliquely below the vial such that at least abnormal contents are detectable.

20. The apparatus of claim 15, wherein the second light is at least disposed below a vial bottom such that light can propagate along vial walls and the camera is located obliquely upwardly toward the vial head such that at least defects in a mouth of the vial are detectable.

21. The apparatus of claim 13, wherein the second light is at least disposed laterally of the vial such that light is reflected from the vial head and the camera is located laterally of the vial such that at least defects in the vial head are detectable.

22. The apparatus of claim 13, wherein the cameras are disposed at separate inspection stations, with each inspection station having a different spacial arrangement of the light and camera.

23. The apparatus of claim 22, wherein the inspection stations are spaced about a rotatable table.

24. The apparatus of claim 13, wherein there are a plurality of CCD cameras and lights.

25. Apparatus of claim 13, wherein the chuck includes a lower holder provided with anchor-shaped links adapted to be swung by a pusher and thereby to open and close chuck fingers, an outer shaft, and an inner shaft connected to said pusher and adapted to be vertically moved together with the outer shaft for a predetermined distance, and the inner shaft is thereafter slidably movable independently of said outer shaft.

26. Apparatus of claim 25, further comprising a mechanism for rotationally driving the outer shaft and a mechanism for vertically moving and closing the chuck.

27. Apparatus of claim 26, wherein the mechanism for vertically moving and closing the chuck comprises a combination of a mechanical valve and an air cylinder.

28. Apparatus of claim 13, wherein the apparatus includes an image processor adapted for processing in parallel images picked up by one or more CCD cameras and pixel counts.

* * * * *